(12) United States Patent
Eskling et al.

(10) Patent No.: US 7,763,452 B2
(45) Date of Patent: Jul. 27, 2010

(54) PURIFICATION OF HER-2 VARIANTS

(75) Inventors: Marie Eskling, Horsholm (DK); Klaus Gregorius Nielsen, Soborg (DK)

(73) Assignee: BN Immunotherapeutics, Inc., Mountain View, CA (US)

( * ) Notice: Subject to any disclaimer, the term of this patent is extended or adjusted under 35 U.S.C. 154(b) by 843 days.

(21) Appl. No.: 10/560,961

(22) PCT Filed: Jun. 24, 2004

(86) PCT No.: PCT/DK2004/000451

§ 371 (c)(1),
(2), (4) Date: May 30, 2006

(87) PCT Pub. No.: WO2004/113377

PCT Pub. Date: Dec. 29, 2004

(65) Prior Publication Data

US 2006/0240511 A1    Oct. 26, 2006

Related U.S. Application Data

(60) Provisional application No. 60/482,315, filed on Jun. 25, 2003.

(30) Foreign Application Priority Data

Jun. 25, 2003    (DK) ............................... 2003 00954

(51) Int. Cl.
| | |
|---|---|
| C12N 15/00 | (2006.01) |
| C12N 15/11 | (2006.01) |
| C12N 15/63 | (2006.01) |
| C12N 1/21 | (2006.01) |
| C12N 5/10 | (2006.01) |

(52) U.S. Cl. .................. 435/252.3; 435/69.1; 435/325; 435/254.11; 435/320.1; 435/69.7; 536/23.1; 536/23.4

(58) Field of Classification Search ...................... None
See application file for complete search history.

(56) References Cited

U.S. PATENT DOCUMENTS 5,976,546 A    11/1999    Ruegg et al.

FOREIGN PATENT DOCUMENTS

WO    WO 97/24438 A    7/1997

(Continued)

OTHER PUBLICATIONS

Colangeli, R. et al., "Three-step purification of lipopolysaccharide-free, polyhistidine-tagged recombinant antigens of Myobacterium tuberculosis" Journal of Chromatography B: Biomedical Sciences & Applications, vol. 714, No. 2, Sep. 4, 1998, pp. 223-235.

(Continued)

*Primary Examiner*—Elizabeth C. Kemmerer
(74) *Attorney, Agent, or Firm*—Law Office of Salvatore Arrigo

(57) ABSTRACT

The present invention provides for a novel method for purification of EGFR family proteins obtained from cultures of insect cells. The process comprises subsequent steps of a) diafiltration and exchange of culture medium with buffer, b) immobilized metal affinity chromatography (IMAC), c) size exclusion chromatography (SEC), and d) anion exchange chromatography (AIE). The method also provides for an immunogenic variant of HER-2 protein for which the purification process has been especially adapted, as well as means for the preparation of the variant.

12 Claims, 2 Drawing Sheets

FOREIGN PATENT DOCUMENTS

| WO | WO 00/20027 A | 4/2000 |
| WO | WO 00/44899 A1 | 8/2000 |
| WO | WO 03/087338 A | 10/2003 |

OTHER PUBLICATIONS

Laroche-Traineau, J. et al., "Three-step purification of bacterially expressed human single-chain Fv antibodies for clinical applications" Journal of Chromatography Biomedical Applications, vol. 737, No. 1-2, Jan. 2000, pp. 107-117.

Porath, J., "Immobilized Metal Ion Affinity Chromatography" Protein Expression and Purification, vol. 3, No. 4, Aug. 1992, pp. 263-281.

Ford, Clark F. et al., "Fusion Tails for the Recovery and Purification of Recombinant Proteins", Protein Expression and Purification, vol. 2, 1991, pp. 95-107.

Porath, Jerker et al., "Metal chelate affinity chromatography, a new approach to protein fractionation", Nature, vol. 258, Dec. 18, 1975, pp. 598-599.

Pedersen, John et al., "Removal of N-Terminal Polhyistidine Tags from Recombinant Proteins Using Engineered Aminopeptidases", Protein Expression and Purification, vol. 15, 1999, pp. 389-400.

SEQUENCE LISTING

```
<160> NUMBER OF SEQ ID NOS: 2

<210> SEQ ID NO 1
<211> LENGTH: 5661
<212> TYPE: DNA
<213> ORGANISM: Artificial sequence
<220> FEATURE:
<223> OTHER INFORMATION: Recombinant expression plasmid derived from pMT
<220> FEATURE:
<221> NAME/KEY: polyA_signal
<222> LOCATION: (263)..(268)
<223> OTHER INFORMATION: SV40 late polyadenylation site
<220> FEATURE:
<221> NAME/KEY: misc_feature
<222> LOCATION: (1579)..(2439)
<223> OTHER INFORMATION: Ampicillin resistance gene, encoded by
      complementary strand
<220> FEATURE:
<221> NAME/KEY: promoter
<222> LOCATION: (3050)..(3415)
<223> OTHER INFORMATION: Metallothionein promoter
<220> FEATURE:
<221> NAME/KEY: RBS
<222> LOCATION: (3493)..(3501)
<223> OTHER INFORMATION: Kozak-like sequence
<220> FEATURE:
<221> NAME/KEY: CDS
<222> LOCATION: (3502)..(5592)
<223> OTHER INFORMATION: DNA encoding immunogenic, his-tagged variant of
      human HER-2
<220> FEATURE:
<221> NAME/KEY: sig_peptide
<222> LOCATION: (3502)..(3555)
<223> OTHER INFORMATION: BiP signal sequence
<220> FEATURE:
<221> NAME/KEY: misc_feature
```

-continued

<222> LOCATION: (3556)..(3597)
<223> OTHER INFORMATION: Histidine tag
<220> FEATURE:
<221> NAME/KEY: mat_peptide
<222> LOCATION: (3556)..(5589)
<220> FEATURE:
<221> NAME/KEY: misc_feature
<222> LOCATION: (3598)..(3603)
<223> OTHER INFORMATION: Dipeptidase stop sequence
<220> FEATURE:
<221> NAME/KEY: misc_feature
<222> LOCATION: (3604)..(5589)
<223> OTHER INFORMATION: Gene coding for the hHER2MA5-5DUH protein
<220> FEATURE:
<221> NAME/KEY: misc_feature
<222> LOCATION: (4357)..(4401)
<223> OTHER INFORMATION: Diphtheria toxoid P2 epitope
<220> FEATURE:
<221> NAME/KEY: misc_feature
<222> LOCATION: (5500)..(5562)
<223> OTHER INFORMATION: Diphtheria toxoid P30 epitope

<400> SEQUENCE: 1

```
ggccgctcga gtctagaggg cccttcgaag gtaagcctat ccctaaccct ctcctcggtc     60
tcgattctac gcgtaccggt catcatcacc atcaccattg agtttaaacc cgctgatcag    120
cctcgactgt gccttctaag atccagacat gataagatac attgatgagt ttggacaaac    180
cacaactaga atgcagtgaa aaaaatgctt tatttgtgaa atttgtgatg ctattgcttt    240
atttgtaacc attataagct gcaataaaca agttaacaac aacaattgca ttcattttat    300
gtttcaggtt cagggggagg tgtgggaggt tttttaaagc aagtaaaacc tctacaaatg    360
tggtatggct gattatgatc agtcgacctg caggcatgca agcttggcgt aatcatggtc    420
atagctgttt cctgtgtgaa attgttatcc gctcacaatt ccacacaaca tacgagccgg    480
aagcataaag tgtaaagcct ggggtgccta atgagtgagc taactcacat taattgcgtt    540
gcgctcactg cccgctttcc agtcgggaaa cctgtcgtgc cagctgcatt aatgaatcgg    600
ccaacgcgcg gggagaggcg gtttgcgtat tgggcgctct tccgcttcct cgctcactga    660
ctcgctgcgc tcggtcgttc ggctgcggcg agcggtatca gctcactcaa aggcggtaat    720
acggttatcc acagaatcag gggataacgc aggaaagaac atgtgagcaa aaggccagca    780
aaaggccagg aaccgtaaaa aggccgcgtt gctggcgttt ttccataggc tccgcccccc    840
tgacgagcat cacaaaaatc gacgctcaag tcagaggtgg cgaaacccga caggactata    900
aagataccag gcgtttcccc ctggaagctc cctcgtgcgc tctcctgttc cgaccctgcc    960
gcttaccgga tacctgtccg cctttctccc ttcgggaagc gtggcgcttt ctcatagctc   1020
acgctgtagg tatctcagtt cggtgtaggt cgttcgctcc aagctgggct gtgtgcacga   1080
accccccgtt cagcccgacc gctgcgcctt atccggtaac tatcgtcttg agtccaaccc   1140
ggtaagacac gacttatcgc cactggcagc agccactggt aacaggatta gcagagcgag   1200
gtatgtaggc ggtgctacag agttcttgaa gtggtggcct aactacggct acactagaag   1260
gacagtattt ggtatctgcg ctctgctgaa gccagttacc ttcggaaaaa gagttggtag   1320
ctcttgatcc ggcaaacaaa ccaccgctgg tagcggtggt ttttttgttt gcaagcagca   1380
gattacgcgc agaaaaaaag gatctcaaga agatcctttg atcttttcta cggggtctga   1440
cgctcagtgg aacgaaaact cacgttaagg gattttggtc atgagattat caaaaaggat   1500
cttcacctag atccttttaa attaaaaatg aagttttaaa tcaatctaaa gtatatatga   1560
gtaaacttgg tctgacagtt accaatgctt aatcagtgag gcacctatct cagcgatctg   1620
tctatttcgt tcatccatag ttgcctgact ccccgtcgtg tagataacta cgatacggga   1680
```

```
gggcttacca tctggcccca gtgctgcaat gataccgcga gacccacgct caccggctcc   1740
agatttatca gcaataaacc agccagccgg aagggccgag cgcagaagtg gtcctgcaac   1800
tttatccgcc tccatccagt ctattaattg ttgccgggaa gctagagtaa gtagttcgcc   1860
agttaatagt ttgcgcaacg ttgttgccat tgctacaggc atcgtggtgt cacgctcgtc   1920
gtttggtatg gcttcattca gctccggttc ccaacgatca aggcgagtta catgatcccc   1980
catgttgtgc aaaaaagcgg ttagctcctt cggtcctccg atcgttgtca gaagtaagtt   2040
ggccgcagtg ttatcactca tggttatggc agcactgcat aattctctta ctgtcatgcc   2100
atccgtaaga tgcttttctg tgactggtga gtactcaacc aagtcattct gagaatagtg   2160
tatgcggcga ccgagttgct cttgcccggc gtcaatacgg gataataccg cgccacatag   2220
cagaacttta aaagtgctca tcattggaaa cgttcttcg gggcgaaaac tctcaaggat   2280
cttaccgctg ttgagatcca gttcgatgta acccactcgt gcacccaact gatcttcagc   2340
atcttttact ttcaccagcg tttctgggtg agcaaaaaca ggaaggcaaa atgccgcaaa   2400
aaagggaata agggcgacac ggaaatgttg aatactcata ctcttccttt ttcaatatta   2460
ttgaagcatt tatcagggtt attgtctcat gagcggatac atatttgaat gtatttagaa   2520
aaataaacaa ataggggttc gcgcacatt tccccgaaaa gtgccacctg acgtctaaga   2580
aaccattatt atcatgacat taacctataa aaataggcgt atcacgaggc cctttcgttc   2640
gcgcgtttcg gtgatgacgg tgaaaacctc tgacacatgc agctcccgga cggtcaca    2700 gcttgtctgt aagcggatgc cgggagcaga caagcccgtc agggcgcgtc agcgggtgtt   2760
ggcgggtgtc ggggctggct taactatgcg gcatcagagc agattgtact gagagtgcac   2820
catatgcggt gtgaaatacc gcacagatgc gtaaggagaa ataccgcat caggcgccat   2880 tcgccattca ggctgcgcaa ctgttgggaa gggcgatcgg tgcgggcctc ttcgctatta   2940
cgccagctgc cgaaggggg atgtgctgca aggcgattaa gttgggtaac gccagggttt   3000
tcccagtcac gacgttgtaa aacgacggcc agtgccagtg aattaattcg ttgcaggaca   3060
ggatgtggtg cccgatgtga ctagctcttt gctgcaggcc gtcctatcct ctggttccga   3120
taagagaccc agaactccgg cccccaccg cccaccgcca cccccataca tatgtggtac    3180
gcaagtaaga gtgcctgcgc atgccccatg tgccccacca agagttttgc atcccataca   3240
agtccccaaa gtggagaacc gaaccaattc ttcgcgggca gaacaaaagc ttctgcacac   3300
gtctccactc gaatttggag ccggccggcg tgtgcaaaag aggtgaatcg aacgaaagac   3360
ccgtgtgtaa agccgcgttt ccaaaatgta taaaaccgag agcatctggc caatgtgcat   3420
cagttgtggt cagcagcaaa atcaagtgaa tcatctcagt gcaactaaag gggggatcta   3480
gatcggggta ccaaagtcac c atg aag ttg tgc atc ttg ctg gcc gtc gtg    3531
                         Met Lys Leu Cys Ile Leu Leu Ala Val Val
                             -15              -10 gcc ttc gtg ggc ctg tcg ctg ggc atg aag cac caa cac caa cat caa    3579
Ala Phe Val Gly Leu Ser Leu Gly Met Lys His Gln His Gln His Gln
         -5               -1  1                5 cat caa cat caa cat caa gcc ccc tcc acc caa gtg tgt acc ggc aca    3627
His Gln His Gln His Gln Ala Pro Ser Thr Gln Val Cys Thr Gly Thr
    10              15                      20 gac atg aag ctg cgg ctc cct gcc agt ccc gag acc cac ctg gac atg    3675
Asp Met Lys Leu Arg Leu Pro Ala Ser Pro Glu Thr His Leu Asp Met
25              30              35                      40 ctc cgc cac ctc tac cag ggc tgc cag gtg gtg cag gga aac ctg gaa    3723
Leu Arg His Leu Tyr Gln Gly Cys Gln Val Val Gln Gly Asn Leu Glu
```

-continued

|  |  |  |
|---|---|---|
| ctc acc tac ctg ccc acc aat gcc agc tta agt ttc ctg cag gat atc<br>Leu Thr Tyr Leu Pro Thr Asn Ala Ser Leu Ser Phe Leu Gln Asp Ile<br>            60              65              70 | 3771 |
| cag gag gtg cag ggc tac gtg ctc atc gct cac aac caa gtg agg cag<br>Gln Glu Val Gln Gly Tyr Val Leu Ile Ala His Asn Gln Val Arg Gln<br>    75              80              85 | 3819 |
| gtc cca ctg cag agg ctg cgg att gtg cga ggc acc cag ctc ttt gag<br>Val Pro Leu Gln Arg Leu Arg Ile Val Arg Gly Thr Gln Leu Phe Glu<br>        90              95              100 | 3867 |
| gac aac tat gcc ctg gcc gtg cta gac aat gga gac ccg ctg aac aat<br>Asp Asn Tyr Ala Leu Ala Val Leu Asp Asn Gly Asp Pro Leu Asn Asn<br>105             110             115             120 | 3915 |
| acc acc cct gtc aca ggg gcc tcc cca gga ggc ctg cgg gag ctg cag<br>Thr Thr Pro Val Thr Gly Ala Ser Pro Gly Gly Leu Arg Glu Leu Gln<br>            125             130             135 | 3963 |
| ctt cga agc ctc aca gag atc ttg aaa gga ggg gtc ttg atc cag cgg<br>Leu Arg Ser Leu Thr Glu Ile Leu Lys Gly Gly Val Leu Ile Gln Arg<br>        140             145             150 | 4011 |
| aac ccc cag ctc tgc tac cag gac acg att ttg tgg aag gac atc ttc<br>Asn Pro Gln Leu Cys Tyr Gln Asp Thr Ile Leu Trp Lys Asp Ile Phe<br>    155             160             165 | 4059 |
| cac aag aac aac cag ctg gct ctc aca ctg ata gac acc aac cgc tct<br>His Lys Asn Asn Gln Leu Ala Leu Thr Leu Ile Asp Thr Asn Arg Ser<br>170             175             180 | 4107 |
| cgg gcc tgc cac ccc tgt tct ccg atg tgt aag ggc tcc cgc tgc tgg<br>Arg Ala Cys His Pro Cys Ser Pro Met Cys Lys Gly Ser Arg Cys Trp<br>185             190             195             200 | 4155 |
| gga gag agt tct gag gat tgt cag agc ctg acg cgc act gtc tgt gcc<br>Gly Glu Ser Ser Glu Asp Cys Gln Ser Leu Thr Arg Thr Val Cys Ala<br>            205             210             215 | 4203 |
| ggt ggc tgt gcc cgc tgc aag ggg cca ctg ccc act gac tgc tgc cat<br>Gly Gly Cys Ala Arg Cys Lys Gly Pro Leu Pro Thr Asp Cys Cys His<br>        220             225             230 | 4251 |
| gag cag tgt gct gcc ggc tgc acg ggc ccc aag cac tct gac tgc ctg<br>Glu Gln Cys Ala Ala Gly Cys Thr Gly Pro Lys His Ser Asp Cys Leu<br>    235             240             245 | 4299 |
| gcc tgc ctc cac ttc aac cac agt ggc atc tgt gag ctg cac tgc cca<br>Ala Cys Leu His Phe Asn His Ser Gly Ile Cys Glu Leu His Cys Pro<br>250             255             260 | 4347 |
| gcc ctg gtc cag tac atc aaa gct aac tcc aaa ttc atc ggt atc acc<br>Ala Leu Val Gln Tyr Ile Lys Ala Asn Ser Lys Phe Ile Gly Ile Thr<br>265             270             275             280 | 4395 |
| gag ctg cgg tat aca ttc ggc gcc agc tgt gtg act gcc tgt ccc tac<br>Glu Leu Arg Tyr Thr Phe Gly Ala Ser Cys Val Thr Ala Cys Pro Tyr<br>            285             290             295 | 4443 |
| aac tac ctt tct acg gac gtg gga tcc tgc acc ctc gtc tgc ccc ctg<br>Asn Tyr Leu Ser Thr Asp Val Gly Ser Cys Thr Leu Val Cys Pro Leu<br>        300             305             310 | 4491 |
| cac aac caa gag gtg aca gca gag gat gga aca cag cgg tgt gag aag<br>His Asn Gln Glu Val Thr Ala Glu Asp Gly Thr Gln Arg Cys Glu Lys<br>    315             320             325 | 4539 |
| tgc agc aag ccc tgt gcc cga gtg tgc tat ggt ctg ggc atg gag cac<br>Cys Ser Lys Pro Cys Ala Arg Val Cys Tyr Gly Leu Gly Met Glu His<br>330             335             340 | 4587 |
| ttg cga gag gtg agg gca gtt acc agt gcc aat atc cag gag ttt gct<br>Leu Arg Glu Val Arg Ala Val Thr Ser Ala Asn Ile Gln Glu Phe Ala<br>345             350             355             360 | 4635 |
| ggc tgc aag aag atc ttt ggg agc ctg gca ttt ctg ccg gag agc ttt | 4683 |

-continued

| | | |
|---|---|---|
| Gly Cys Lys Lys Ile Phe Gly Ser Leu Ala Phe Leu Pro Glu Ser Phe<br>365     370     375 | | |
| gat ggg gac cca gcc tcc aac act gcc ccg ctc cag cca gag cag ctc<br>Asp Gly Asp Pro Ala Ser Asn Thr Ala Pro Leu Gln Pro Glu Gln Leu<br>380     385     390 | 4731 | |
| caa gtg ttt gag act ctg gaa gag atc aca ggt tac cta tac atc tca<br>Gln Val Phe Glu Thr Leu Glu Glu Ile Thr Gly Tyr Leu Tyr Ile Ser<br>395     400     405 | 4779 | |
| gca tgg ccg gac agc ctg cct gac ctc agc gtc ttc cag aac ctg caa<br>Ala Trp Pro Asp Ser Leu Pro Asp Leu Ser Val Phe Gln Asn Leu Gln<br>410     415     420 | 4827 | |
| gta atc cgg gga cga att ctg cac aat ggc gcc tac tcg ctg acc ctg<br>Val Ile Arg Gly Arg Ile Leu His Asn Gly Ala Tyr Ser Leu Thr Leu<br>425     430     440 | 4875 | |
| caa ggg ctg ggc atc agc tgg ctg ggg ctg cgc tca ctg agg gaa ctg<br>Gln Gly Leu Gly Ile Ser Trp Leu Gly Leu Arg Ser Leu Arg Glu Leu<br>445     450     455 | 4923 | |
| ggc agt gga ctg gcc ctc atc cac cat aac acc cac ctc tgc ttc gtg<br>Gly Ser Gly Leu Ala Leu Ile His His Asn Thr His Leu Cys Phe Val<br>460     465     470 | 4971 | |
| cac acg gtg ccc tgg gac cag ctc ttt cgg aac ccg cac caa gct ctg<br>His Thr Val Pro Trp Asp Gln Leu Phe Arg Asn Pro His Gln Ala Leu<br>475     480     485 | 5019 | |
| ctc cac act gcc aac cgg cca gag gac gag tgt gtg ggc gag ggc ctg<br>Leu His Thr Ala Asn Arg Pro Glu Asp Glu Cys Val Gly Glu Gly Leu<br>490     495     500 | 5067 | |
| gcc tgc cac cag ctg tgc gcc cga ggg cac tgc tgg ggt cca ggg ccc<br>Ala Cys His Gln Leu Cys Ala Arg Gly His Cys Trp Gly Pro Gly Pro<br>505     510     515     520 | 5115 | |
| acc cag tgt gtc aac tgc agc cag ttc ctt cgg ggc cag gag tgc gtg<br>Thr Gln Cys Val Asn Cys Ser Gln Phe Leu Arg Gly Gln Glu Cys Val<br>525     530     535 | 5163 | |
| gag gaa tgc cga gta ctg cag ggg ctc ccc agg gag tat gtg aat gcc<br>Glu Glu Cys Arg Val Leu Gln Gly Leu Pro Arg Glu Tyr Val Asn Ala<br>540     545     550 | 5211 | |
| agg cac tgt ttg ccg tgc cac cct gag tgt cag ccc cag aat ggc tca<br>Arg His Cys Leu Pro Cys His Pro Glu Cys Gln Pro Gln Asn Gly Ser<br>555     560     565 | 5259 | |
| gtg acc tgt ttt gga ccg gag gct gac cag tgt gtg gcc tgt gcc cac<br>Val Thr Cys Phe Gly Pro Glu Ala Asp Gln Cys Val Ala Cys Ala His<br>570     575     580 | 5307 | |
| tat aag gac cct ccc ttc tgc gtg gcc cgc tgc ccc agc ggt gtg aaa<br>Tyr Lys Asp Pro Pro Phe Cys Val Ala Arg Cys Pro Ser Gly Val Lys<br>585     590     595     600 | 5355 | |
| cct gac ctc tcc tac atg ccc atc tgg aag ttt cca gat gag gag ggc<br>Pro Asp Leu Ser Tyr Met Pro Ile Trp Lys Phe Pro Asp Glu Glu Gly<br>605     610     615 | 5403 | |
| gca tgc cag cct tgc ccc atc aac tgc acc cac tcc tgt gtg gac ctg<br>Ala Cys Gln Pro Cys Pro Ile Asn Cys Thr His Ser Cys Val Asp Leu<br>620     625     630 | 5451 | |
| gat gac aag ggc tgc ccc gcc gag cag aga gcc agc cct ctg acg tcc<br>Asp Asp Lys Gly Cys Pro Ala Glu Gln Arg Ala Ser Pro Leu Thr Ser<br>635     640     645 | 5499 | |
| ttc aac aac ttc acc gtg agc ttc tgg ctg cgc gtg ccc aag gtg agc<br>Phe Asn Asn Phe Thr Val Ser Phe Trp Leu Arg Val Pro Lys Val Ser<br>650     655     660 | 5547 | |
| gcc agc cac ctg gag atc gtc tct gcg gtg gtt ggc att ctg<br>Ala Ser His Leu Glu Ile Val Ser Ala Val Val Gly Ile Leu<br>665     670     675 | 5589 | |

```
tagaagcttg gtaccgagct cggatccact agtccagtgt ggtggaattc tgcagatatc     5649
cagcacagtg gc                                                         5661
```

<210> SEQ ID NO 2
<211> LENGTH: 696
<212> TYPE: PRT
<213> ORGANISM: Artificial sequence
<220> FEATURE:
<223> OTHER INFORMATION: Recombinant expression plasmid derived from pSI

<400> SEQUENCE: 2

```
Met Lys Leu Cys Ile Leu Leu Ala Val Val Ala Phe Val Gly Leu Ser
            -15                 -10                  -5

Leu Gly Met Lys His Gln His Gln His Gln His Gln His Gln His Gln
    -1   1               5                  10

Ala Pro Ser Thr Gln Val Cys Thr Gly Thr Asp Met Lys Leu Arg Leu
 15              20                  25                  30

Pro Ala Ser Pro Glu Thr His Leu Asp Met Leu Arg His Leu Tyr Gln
                 35                  40                  45

Gly Cys Gln Val Val Gln Gly Asn Leu Glu Leu Thr Tyr Leu Pro Thr
             50                  55                  60

Asn Ala Ser Leu Ser Phe Leu Gln Asp Ile Gln Glu Val Gln Gly Tyr
 65                  70                  75

Val Leu Ile Ala His Asn Gln Val Arg Gln Val Pro Leu Gln Arg Leu
 80                  85                  90

Arg Ile Val Arg Gly Thr Gln Leu Phe Glu Asp Asn Tyr Ala Leu Ala
 95             100                 105                 110

Val Leu Asp Asn Gly Asp Pro Leu Asn Asn Thr Thr Pro Val Thr Gly
                115                 120                 125

Ala Ser Pro Gly Gly Leu Arg Glu Leu Gln Leu Arg Ser Leu Thr Glu
            130                 135                 140

Ile Leu Lys Gly Gly Val Leu Ile Gln Arg Asn Pro Gln Leu Cys Tyr
            145                 150                 155

Gln Asp Thr Ile Leu Trp Lys Asp Ile Phe His Lys Asn Asn Gln Leu
    160                 165                 170

Ala Leu Thr Leu Ile Asp Thr Asn Arg Ser Arg Ala Cys His Pro Cys
175                 180                 185                 190

Ser Pro Met Cys Lys Gly Ser Arg Cys Trp Gly Glu Ser Ser Glu Asp
                195                 200                 205

Cys Gln Ser Leu Thr Arg Thr Val Cys Ala Gly Gly Cys Ala Arg Cys
            210                 215                 220

Lys Gly Pro Leu Pro Thr Asp Cys Cys His Glu Gln Cys Ala Ala Gly
            225                 230                 235

Cys Thr Gly Pro Lys His Ser Asp Cys Leu Ala Cys Leu His Phe Asn
    240                 245                 250

His Ser Gly Ile Cys Glu Leu His Cys Pro Ala Leu Val Gln Tyr Ile
255                 260                 265                 270

Lys Ala Asn Ser Lys Phe Ile Gly Ile Thr Glu Leu Arg Tyr Thr Phe
                275                 280                 285

Gly Ala Ser Cys Val Thr Ala Cys Pro Tyr Asn Tyr Leu Ser Thr Asp
            290                 295                 300

Val Gly Ser Cys Thr Leu Val Cys Pro Leu His Asn Gln Glu Val Thr
            305                 310                 315

Ala Glu Asp Gly Thr Gln Arg Cys Glu Lys Cys Ser Lys Pro Cys Ala
            320                 325                 330
```

-continued

```
Arg Val Cys Tyr Gly Leu Gly Met Glu His Leu Arg Glu Val Arg Ala
335                 340                 345                 350
Val Thr Ser Ala Asn Ile Gln Glu Phe Ala Gly Cys Lys Lys Ile Phe
            355                 360                 365
Gly Ser Leu Ala Phe Leu Pro Glu Ser Phe Asp Gly Asp Pro Ala Ser
            370                 375                 380
Asn Thr Ala Pro Leu Gln Pro Glu Gln Leu Gln Val Phe Glu Thr Leu
            385                 390                 395
Glu Glu Ile Thr Gly Tyr Leu Tyr Ile Ser Ala Trp Pro Asp Ser Leu
        400                 405                 410
Pro Asp Leu Ser Val Phe Gln Asn Leu Gln Val Ile Arg Gly Arg Ile
415                 420                 425                 430
Leu His Asn Gly Ala Tyr Ser Leu Thr Leu Gln Gly Leu Gly Ile Ser
                435                 440                 445
Trp Leu Gly Leu Arg Ser Leu Arg Glu Leu Gly Ser Gly Leu Ala Leu
            450                 455                 460
Ile His His Asn Thr His Leu Cys Phe Val His Thr Val Pro Trp Asp
        465                 470                 475
Gln Leu Phe Arg Asn Pro His Gln Ala Leu Leu His Thr Ala Asn Arg
    480                 485                 490
Pro Glu Asp Glu Cys Val Gly Glu Gly Leu Ala Cys His Gln Leu Cys
495                 500                 505                 510
Ala Arg Gly His Cys Trp Gly Pro Gly Pro Thr Gln Cys Val Asn Cys
                515                 520                 525
Ser Gln Phe Leu Arg Gly Gln Glu Cys Val Glu Glu Cys Arg Val Leu
            530                 535                 540
Gln Gly Leu Pro Arg Glu Tyr Val Asn Ala Arg His Cys Leu Pro Cys
        545                 550                 555
His Pro Glu Cys Gln Pro Gln Asn Gly Ser Val Thr Cys Phe Gly Pro
    560                 565                 570
Glu Ala Asp Gln Cys Val Ala Cys Ala His Tyr Lys Asp Pro Pro Phe
575                 580                 585                 590
Cys Val Ala Arg Cys Pro Ser Gly Val Lys Pro Asp Leu Ser Tyr Met
                595                 600                 605
Pro Ile Trp Lys Phe Pro Asp Glu Glu Gly Ala Cys Gln Pro Cys Pro
            610                 615                 620
Ile Asn Cys Thr His Ser Cys Val Asp Leu Asp Asp Lys Gly Cys Pro
        625                 630                 635
Ala Glu Gln Arg Ala Ser Pro Leu Thr Ser Phe Asn Asn Phe Thr Val
    640                 645                 650
Ser Phe Trp Leu Arg Val Pro Lys Val Ser Ala Ser His Leu Glu Ile
655                 660                 665                 670
Val Ser Ala Val Val Gly Ile Leu
                675
```

PURIFICATION OF HER-2 VARIANTS

FIELD OF THE INVENTION

The present invention relates to the field of affinity purification of proteins. More particularly, the present invention relates to improvements in metal affinity protein purification, especially purification of histidine tagged or histidine rich proteins that have been recombinantly produced in insect cells. The invention also relates to specific purification schemes suitable for histidine-tagged protein variants derived from the EGFR (endothelial growth factor receptor) family of proteins, especially the cancer-associated antigen HER-2.

Further, the present invention relates to an immunogenic variant of human HER-2 that is capable of raising an immune response in humans, which also targets the native human HER-2 molecule.

BACKGROUND OF THE INVENTION

The cancer associated membrane protein HER-2 is a member of the EGFR family of proteins. This particular protein has shown promise as an immunogen in active specific immunotherapy of certain cancers, notably breast cancer and colorectal cancer.

The assignee of the present patent application has previously filed patent applications relating to active vaccination against the HER-2 antigen, cf. WO 00/20027 which is hereby incorporated by reference herein. Further research in this field has now identified preferred HER-2 variants for such vaccines, but a general problem in protein chemistry is to devise improved means for obtaining satisfactory yields of recombinant protein with a high degree of purity.

Immobilized metal ion affinity chromatography (IMAC) was first introduced by Porath (Porath, J., J. Carlsson, I. Olsson, G. Belfrage [1975] Nature 258:598-599) under the term metal chelate chromatography and has been previously reviewed in several articles (Porath, J. [1992] Protein Purification and Expression 3:263-281; and articles cited therein). The IMAC purification process is based on the employment of a chelating matrix loaded with soft metal ions such as $Cu^{2+}$ and $Ni^{2+}$. Electron-donating groups on the surface of proteins, especially the imidazole side chain of histidine, can bind to the non-coordinated sites of the loaded metal. The interaction between the electron donor group with the metal can be made reversible by lowering the pH or by displacement with imidazole. Thus, a protein possessing electron-donating groups such as histidine can be purified by reversible metal complex/protein interactions.

In 1991, Ford et al. (Ford, C., I. Suominen, C. Glatz [1991] Protein Expression and Purification 2:95-107) described protein purification using IMAC technology (Ni-NTA ligand) as applied to recombinant proteins having tails with histidine residues (polyhistidine recombinant proteins, "His-tagged proteins"). This method takes advantage of the fact that two or more histidine residues can cooperate to form very strong metal ion complexes.

Numerous variations of this technology exists, where the histidine residues are attached as "tags" to the relevant recombinant protein in various combinations, e.g. including recognition sites for specific proteases so that the his tag can be subsequently removed enzymatically.

Expression of proteins in insect cells require the use of various specialised culture media and also entails contamination of the recombinant protein with various insect cell derived constituents that are not found in bacteria, fungi and mammalian cells. Purification schemes devised for recombinant proteins produced in bacteria, fungi, or mammalian cells are therefore not necessarily the optimum choice when a protein produced in insect cells will need to be purified.

There is therefore a continuing need for improvements in protein purification in order to obtain pharmaceutical grade protein derived from recombinant production in insect cells.

OBJECT OF THE INVENTION

It is an object of the invention to provide an improved method for purifying recombinant EGFR family protein expressed in insect cells. It is a further object of the invention to provide an immunogenic variant of HER-2 protein that is useful in e.g. cancer treatment by means of specific active immunotherapy.

SUMMARY OF THE INVENTION

The present inventors have devised a novel method for purifying EGFR family protein to a degree of purity, which is acceptable for pharmaceutical use, notably for use as vaccine agents.

Hence, in one aspect, the present invention relates to a method for purification of an EGFR family derived protein, said protein being recombinantly produced in an insect cell culture and said protein being one that is suitable for purification by means of immobilised metal affinity chromatography, the method comprising obtaining, from said insect cell culture, a substantially cell-free sample containing said EGFR family derived protein, and thereafter enriching for said EGFR family derived protein by means of subsequent steps of:

- diafiltration and exchange of culture medium with buffer,
- immobilized metal affinity chromatography (IMAC),
- size exclusion chromatography (SEC), and
- anion exchange chromatography (AIE).

Another aspect of the invention relates to an immunogenic variant of HER-2 protein that comprises the amino acid sequence set forth in SEQ ID NO: 2, residues 17-677.

The arrow indicates the 104.1 peak.

Figure 2:
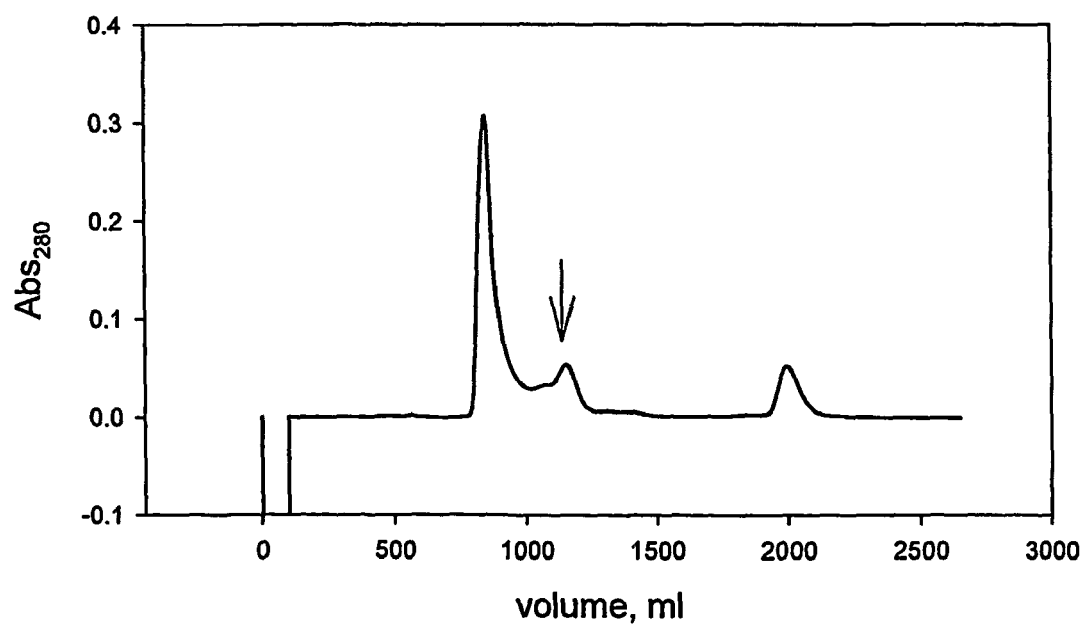

FIG. 2: Chromatographic profile of the SEC.

The arrow indicates the monomer peak.

Figure 3:
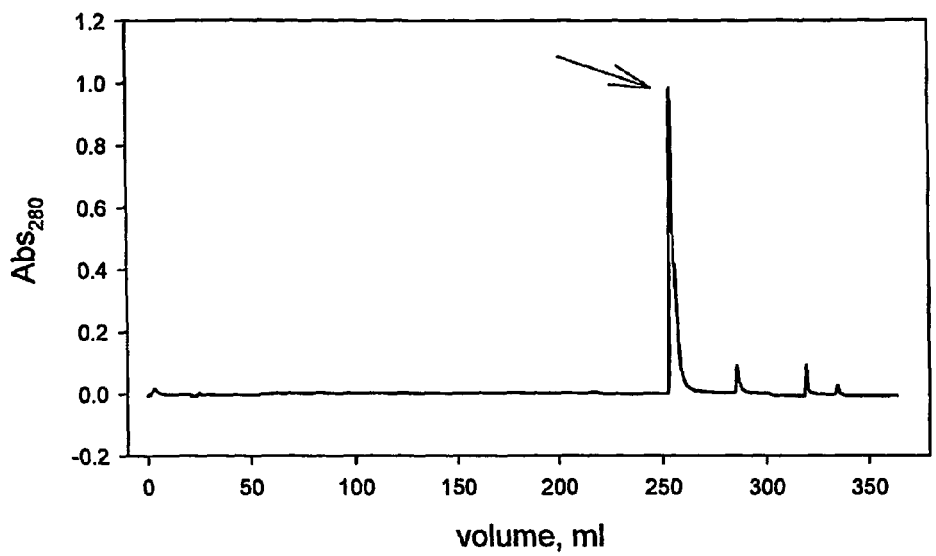

FIG. 3: Chromatographic profile of the AIE.

The arrow indicates the 104.1 peak.

Figure 4:
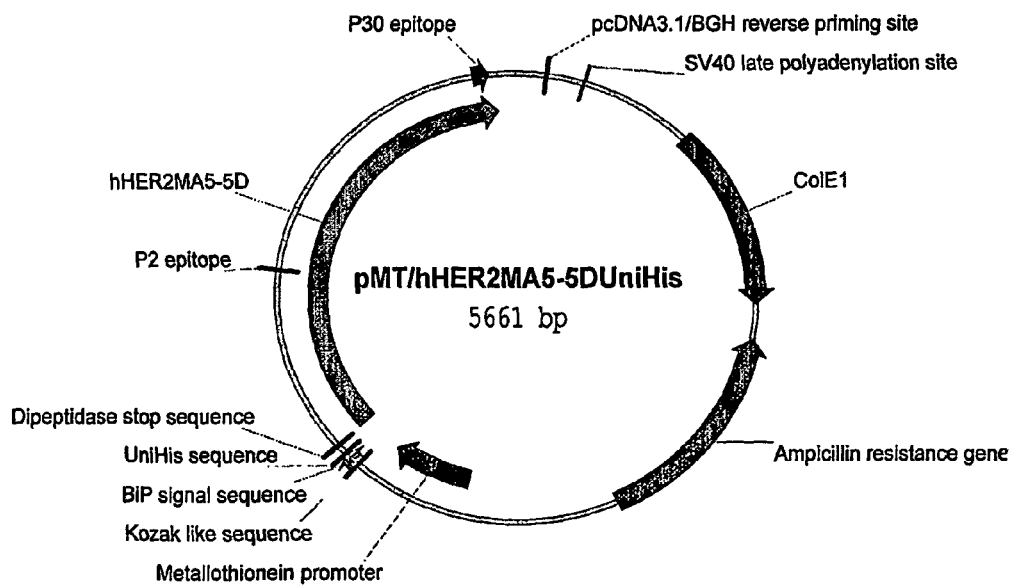

FIG. 4: The pMT/hHER2MA5-5DUniHis vector p992, plasmid map. hHER2MA5-5D: Gene coding for the hHER2MA5-5DUH protein (nucleotides 3604-5592).

P2 epitope: Sequence coding for the P2 epitope in the hHER2MA5-5DUH protein (nucleotides 4357-4401).

P30 epitope: Sequence coding for the P30 epitope in the hHER2MA5-5DUH protein (nucleotides 5500-5562).

SV40 late Polyadenylation site: Poly A signal (nucleotides 263-268).

ColE1: Origin of replication for replication in *E. coli* (nucleotides 701-1434).

Ampicillin resistance gene: Gene conferring ampicillin resistance in bacteria (nucleotides 1579-2439).

Metallothionein promoter: Promoter that can be induced with a number of compounds (e.g. cadmium) (nucleotides 3050-3415).

Kozak like sequence: Ribosomal binding site (nucleotides 3493-3501).

BiP signal sequence: Signal sequence directing the HER2 variant protein to secretion into the extracellular compartment (nucleotides 3502-3555).

UniHis sequence: Sequence coding for the UniHis tag used for purification of the HER2 AutoVac protein (nucleotides 3556-3597).

Dipeptidase stop sequence: Used if the UniHis tag is to be cleaved from the HER2 AutoVac protein (nucleotides 3598-3603).

DETAILED DISCLOSURE OF THE INVENTION

In the following a number of terms and expressions will be defined in the context of the present invention.

"An EGFR family derived protein" denotes a protein which is homologous to or identical with human EGFR (or ErbB-1); human HER-2/neu (ErbB-2); HER-3 (ErbB-3); or HER-4 (ErbB-4).

An "autologous" EGFR family protein is in the present specification and claims intended to denote an EGFR family polypeptide of an animal that is going to be vaccinated against its own EGFR family protein. In other words, the term is only relevant when the relation to the animal that it going to be vaccinated is considered.

The terms "T-lymphocyte" and "T-cell" will be used interchangeably for lymphocytes of thymic origin which are responsible for various cell mediated immune responses as well as for effector functions such as helper activity in the humeral immune response. Likewise, the terms "B-lymphocyte" and "B-cell" will be used interchangeably for antibody-producing lymphocytes.

An "antigen presenting cell" (APC) is a cell which presents epitopes to T-cells. Typical antigen-presenting cells are macrophages, dendritic cells and other phagocytizing and pinocytizing cells. It should be noted that B-cells also functions as APCs by presenting $T_H$ epitopes bound to MCH class II molecules to $T_H$ cells but when generally using the term APC in the present specification and claims it is intended to refer to the above-mentioned phagocytizing and pinocytizing cells.

"Helper T-lymphocytes" or "$T_H$ cells" denotes CD4 positive T-cells, which provide help to B-cells and cytotoxic T-cells via the recognition of $T_H$ epitopes bound to MHC Class II molecules on antigen presenting cells.

The term "cytotoxic T-lymphocyte" (CTL) will be used for CD8 positive T-cells, which require the assistance of $T_H$ cells in order to become activated.

A "specific" immune response is in the present context intended to denote a polyclonal immune response directed predominantly against a molecule or a group of quasi-identical molecules or, alternatively, against cells which present CTL epitopes of the molecule or the group of quasi-identical molecules.

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively.

By the term "down-regulation an autologous EGFR family protein" is herein meant reduction in the living organism of the amount and/or activity of the relevant EGFR family protein. The down-regulation can be obtained by means of several mechanisms including removal of the CEA by scavenger cells (such as macrophages and other phagocytizing cells), and even more important, that cells carrying or harbouring the antigen are killed by CTLs in the animal.

The term "immunogen" is intended to denote a substance capable of inducing an immune response in a certain animal. It will therefore be understood that an autologous EGFR family protein is not an immunogen in the autologous host—it is necessary to use either a strong adjuvant and/or to co-present T helper epitopes with the autologous protein in order to mount an immune response against autologous protein and in such a case the "immunogen" is the composition of matter which is capable of breaking autotolerance.

The term "immunogenically effective amount" has its usual meaning in the art, i.e. an amount of an immunogen, which is capable of inducing an immune response, which significantly engages pathogenic agents, which share immunological features with the immunogen.

The term "pharmaceutically acceptable" has its usual meaning in the art, i.e. it is used for a substance that can be accepted as part of a medicament for human use when treating the disease in question and thus the term effectively excludes the use of highly toxic substances that would worsen rather than improve the treated subject's condition.

A "foreign T-cell epitope" is a peptide which is able to bind to an MHC molecule and which stimulates T-cells in an animal species. Preferred foreign epitopes are "promiscuous" epitopes, i.e. epitopes, which binds to a substantial fraction of MHC class II molecules in an animal species or population. A term, which is often used interchangeably in the art, is the term "universal T-cell epitopes" for this kind of epitopes. Only a very limited number of such promiscuous T-cell epitopes are known, and they will be discussed in detail below. It should be noted that in order for the immunogens which are used according to the present invention to be effective in as large a fraction of an animal population as possible, it may be necessary to 1) insert several foreign T-cell epitopes in the same analogue or 2) prepare several analogues wherein each analogue has a different promiscuous epitope inserted. It should be noted that the concept of foreign T-cell epitopes also encompasses use of cryptic T-cell epitopes, i.e. epitopes which are derived from a self-protein and which only exerts immunogenic behaviour when existing in isolated form without being part of the self-protein in question.

"foreign T helper lymphocyte epitope" (a foreign $T_H$ epitope) is a foreign T cell epitope, which binds an MHC Class II molecule and can be presented on the surface of an antigen presenting cell (APC) bound to the MHC Class II molecule. It is also important to add that the "foreignness" feature therefore has two aspects: A foreign $T_H$ epitope is 1) presented in the MHC Class II context by the animal in question and 2) the foreign epitope is not derived from the same polypeptide as the target antigen for the immunization—the epitope is thus also foreign to the target antigen.

A "CTL epitope" is a peptide, which is able to bind to an MHC class I molecule.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Diafiltration" is a technique using ultrafiltration membranes to remove salt or solvent, exchange buffers, or fractionate different size biomolecules in macromolecular solutions. Macromolecules retained by the ultrafiltration membrane are concentrated while solvent and lower molecular weight species are removed. However, a simple concentration of the macromolecular sample will not completely remove the smaller species. Therefore, the smaller species must be "washed" from the sample using multiple wash volumes (diafiltration). After the diafiltration process, the sample can be concentrated for further analysis or purification. This is an advantage compared with gel filtration or dialysis when the sample can be diluted during the separation process, requiring an additional concentration step. There is no loss or contamination using diafiltration as could occur with a two-step process.

"Immobilised metal affinity chromatography" (IMAC) is a chromatographic technique where proteins are purified as a consequence of their affinity for certain divalent metal ions, cf. the description in the "Background of the Invention".

"Size exclusion chromatography" (SEC) is a chromatographic technique, where proteins and other macromolecules are fractionated according to their physical size. Small molecules are retained in pores of the matrix and are therefore eluted slowly, whereas larger molecules are excluded and therefore eluted early from the matrix.

"Anion Exchange Chromatography" (AIE) is a chromatographic technique, where molecules having a net negative charge are retained on the column matrix and subsequently eluted by displacing with anion from the elution buffer or by changing net charge of the protein.

DESCRIPTION OF THE PREFERRED EMBODIMENTS

The present invention relates to a purification process that is especially tailored for purification of EGFR family derived proteins that have been produced recombinantly in insect cells. The present invention was conceived in connection with efforts that have led to the preparation of immunogenic variants of the human cancer-associated antigen HER-2—these variants are produced in the DES® expression system, an expression system owned by GlaxoSmithKline and marketed by i.a. Invitrogen. The system utilises S2 *Drosophila* cells and specialised vectors. The use of S2 cells as host cells for recombinant production has, however, posed its own set of problems to solve vis-à-vis the HER-2 variant in question, and these problems have been solved by using the inventive method (i.a. problems with co-migrating proteins which are derived from the S2 cells).

The particular protein that is used in the Examples is a variant of human HER-2, which is immunogenic in humans—the variant includes the amino acid sequence set forth in SEQ ID NO: 2, residues 17-677. However, since this amino acid sequence is not in itself suitable for IMAC, it contains an N-terminal histidine tag (amino acid residues 1-14 in SEQ ID NO: 1) that can be cleaved off by an amino-dipeptidase (dipeptidyl peptidase I, DPPI, cf. Pedersen J et al., 1999, Protein Expression and Purification 15, 389-400). The stop sequence for the diaminopeptidase consists of residues 15 and 16 in SEQ ID NO: 2.

Therefore, in general the instant purification method is especially suited for EGFR family derived proteins that include a heterologous amino acid sequence that facilitates purification by means of IMAC. This sequence may be native to the EGFR family derived protein, but more often it is heterologous amino acid sequence (i.e. not naturally associated with the EGFR family derived protein). Preferred amino acid sequences for this purpose are rich in histidine residues (e.g. the $His_6$ tag and other amino acid sequences with several consecutive histidine residues). The most preferred heterologous amino acid sequence that facilitates IMAC purification is the one comprising residues 1-14 of SEQ ID NO: 2.

The EGFR derived protein subjected to the inventive process is preferably one that comprises a substantial part of the amino acid sequence of human EGFR or human HER-2, and it is especially preferred the this substantial part is mainly derived from the extracellular portion of human EGFR or human HER-2.

Most preferred is a variant of human HER-2, and in the most preferred embodiments, the variant of human HER-2 includes at least one foreign T helper cell epitope.

As mentioned above, the inventive process has been conceived in connection with work on recombinant production of certain variants of human HER-2 antigen. These variants are characteristic in including promiscuous foreign T-helper epitopes that are introduced into the amino acid sequence of human HER-2 extracellular domain. Preferred variants of human HER-2 include tetanus toxoid epitopes P2 (residues 269-282 of SEQ ID NO: 2) and P30 (residues 649-669 of SEQ ID NO: 2) and the most preferred variant has an amino acid sequence that consists of residues 1-677 of SEQ ID NO: 2

Diafiltration/Buffer Exchange

The step of diafiltration/buffer exchange is performed at a temperature from about 2 to about 25° C. However, preferably temperatures in the lower part of the range are used, e.g. temperatures below 20° C., such as below 15° C. or below 10° C. Most preferred temperatures are in the range between 2 and 9° C., such as in the range between about 3° C. and about 9° C., with a most preferred temperature range from about 3 to about 8 and especially preferred from 4 to about 6° C. At higher temperatures (e.g. beyond 10° C.) there is a tendency that the protein aggregates, and this can be counteracted by adding a detergent, such as a Tween type detergent.

Normally, the diafiltration is performed in two rounds so as to initially concentrate macromolecular compounds in the sample of culture medium and thereafter to exchange culture medium with buffer. These procedures are done following standard procedures in the art, cf. also the examples. It is preferred that the concentration step results in a concentration of between 2 and 25 times of the macromolecular compounds, such as a concentration between 2 and 20 times, 3 and 15 times, between 3 and 10 times. Preferred concentration of macromolecular compounds is in the range of between 4 and 8 times, and the most preferred concentration is about 5 times or to a total protein concentration of the medium not exceeding 3 mg/ml, or preferably not exceeding 2 mg/ml.

The buffer exchange is typically performed in two subsequent steps of which the first takes place at a pH of at least 6.5 and at most 7.2 and of which the second takes place at a pH of at least 7.0 and of most 8.0. It is, however, possible to perform both steps at the same pH in the overlapping part of the two ranges. Typically, the buffer exchange is performed using a phosphate buffer.

After completion of the buffer exchange, the stringency of the following steps is preferably increased by adding an agent to the sample that will compete for binding to the chromatographic matrix in the IMAC step so as to reduce the amount of non-significant binding by contaminating constituents. For example, addition of imidazole, histidine or a high salt concentration buffer to the diafiltrated and buffer can be done to increase the stringency. Preferably, when imidazole is used, it is added so as to reach a concentration in the range between about 0.05 to about 20 mM, preferably in the range from about 0.5 to about 15 mM, such as in the range from about 1 to about 10 mM. Especially preferred is concentration of imidazole in the range from about 2 to about 9 mM, such as a concentration from about 3 to about 8 mM. most preferred is an imidazole concentration of about 4 to about 6 mM, such as a concentration about 5 mM.

When using a high salt concentration buffer (often NaCl), the concentration is in the range from 100 mM up to about 1 M.

It is also preferred to add a detergent to the diafiltrated and buffer changed sample prior to the IMAC step. The detergent will normally be selected from a polyoxyethylene sorbitan fatty acid ester such as Tween 20, Tween 40, Tween 60, Tween 80, and Tween 85, an alkylaryl polyether alcohol such as Triton X100, a non-ionic detergent, and a carbohydrate based detergent such as octylglycoside. The detergent is advantageously added to reach a concentration of between about 0.05% (v/v) and 10% (v/v), such as about 0.1% (v/v).

IMAC

The IMAC step involves charging of a chromatographic medium with a divalent metal ion prior to application of the buffer exchanged sample thereto. Typically, the divalent metal ion is selected from the group consisting of $Ni^{2+}$, $Cu^{2+}$, $Zn^{2+}$, $Co^{2+}$, and $Fe^{2+}$. Preferably, the divalent metal ion is $Zn^{2+}$.

Elution of the chromatographic medium in the IMAC is performed by applying imidazole, histidine, a high salt concentration buffer, or a change of pH onto the chromatographic medium (typically in a chromatographic column). For instance, when using imidazole for elution, this is advantageously done by applying the imidazole in one single step at a concentration between about 50 mM and about 500 mM (such as between 100 and 400 mM), preferably at a concentration of about 200 mM. Alternatively, when histidine is used this is done by applying the histidine in one single step at a concentration between about 20 mM and 400 mM (such as between 50 and 200 mM), preferably about 100 mM. The high salt concentration buffer usually contains NaCl in concentrations up to about 1 or even 2 M.

SEC

The average pore size of the SEC matrix is preferably one that separates globular protein between 10 kDa and 600 kDa.

After having applied the sample to the matrix, elution is done with a phosphate or TRIS buffer or, alternatively, with a biological buffer such as HEPES. The preferred buffer is a TRIS buffer.

pH is maintained in the range of about 7 to about 8 during the SEC and preferably the pH is kept about 7.5.

If relevant and necessary (i.e. when a phosphate buffer is used in the SEC step), samples containing the EGFR family derived protein obtained from SEC, is diluted before the AIE step so as to adjust the phosphate concentration to less than 15 mM, such as to the range between 10 and 12.5 mM. However, it is surprising that the AIE can be performed at all using such a phosphate buffer concentration.

AIE

The final step in the purification procedure of the invention is at least one AIE step, whereof one is performed using a strong anion exchange matrix—in preferred embodiments, there is also a preceding step involving use of a weak anion exchange matrix. This preferably involves loading of the sample containing the EGFR family derived protein obtained after SEC on a strong or weak anion exchange matrix. Typically, the elution is performed with a buffered (phosphate, TRIS or a biological buffer such as HEPES) NaCl solution at a pH between 7 and 8, preferably about pH 7.5.

The protein obtained in the eluate after these steps has a clinical grade purity and is substantially free of contaminants derived from the insect cell culture.

It is contemplated that an AIE step utilising a weak anion exchange matrix will be applicable as a step between the IMAC and SEC steps, instead of including it as part of the concluding AIE step.

Further Optional Steps

After diafiltration it is advantageous to include a virus clearance step (e.g. with 2% Tween 20 and 0.3% TnBP) and it is further advantageous to include a virus filtration step after AIE (e.g. using a Planova 15N filter or a similar filter), where both steps are included in order to ensure that the resulting product is free of clinically unacceptable contaminants. However, in the event a virus-free system is employed, these two steps are non-essential.

HER-2 Variant of the Invention

As mentioned above, the present inventive method has been conceived when purifying a variant of the human HER-2 tumour antigen. This particular variant has proven to be especially well-suited as a vaccine agent for inducing immunological reactions against autologous HER-2 so this particular variant is also a part of the present invention.

In general, the specific use, formulation, recombinant production, suitable vectors and host cells as well as other details pertaining to this specific HER-2 variant can be found in the disclosure of WO 00/20027. Hence, in the following only a brief discussion will be provided that specifically pertains to the variant. Hence, the disclosure of WO 00/20027 is included by reference herein and provides for the necessary teachings concerning immunization with HER-2 variants and the general methods for producing these and their formulation. Also the disclosure in WO 00/20027 relating to nucleic acid vaccination against autologous HER-2 is incorporated by reference herein.

As mentioned above, another aspect of the present invention relates to an immunogenic variant of HER-2 protein that comprises the amino acid sequence set forth in SEQ ID NO: 2, residues 17-677. It is preferred that this variant is a polypeptide that consists of the amino acid sequence set forth in SEQ ID NO: 2, residues 1-677, i.e. a variant that also includes a histidinyl-rich purification tag consisting of residues 1-14 in SEQ ID NO: 2, and an aminopeptidase stop sequence consisting of residues 15 and 16 in SEQ ID NO: 2.

Also included in the present invention is a nucleic acid fragment that encodes this immunogenic variant of HER-2 protein, such as a DNA fragment. An especially preferred DNA fragment has the HER-2 variant encoding sequence set forth in SEQ ID NO: 1.

Useful tools in the recombinant production of HER-2 variants are vectors carrying the nucleic acid fragment of the invention. Especially preferred is a vector capable of autonomous replication. Typically, the vector is selected from the group consisting of a plasmid, a phage, a cosmid, a minichromosome, and a virus.

Expression vectors are especially preferred. A typical expression vector of the invention comprises, in the 5'→3' direction and in operable linkage, a promoter for driving expression of the nucleic acid fragment of the invention, optionally a nucleic acid sequence encoding a leader peptide enabling secretion of or integration into the membrane of the polypeptide fragment, the nucleic acid fragment of the invention, and optionally a nucleic acid sequence encoding a terminator.

For recombinant production, a host cell transformed with the vector of the invention is especially preferred. A particularly interesting host cell is an insect cell, and most preferred is a *drosophila* derived host cell such, as an S2 cell.

Also part of the invention is a stable cell line which carries the vector of the invention and which expresses the nucleic acid fragment of the invention, and which optionally secretes or carries on its surface the immunogenic variant of HER-2 protein of the invention.

Furthermore, the invention also provides for an immunogenic composition for immunizing against HER-2 protein in a human comprising the immunogenic variant of HER-2 protein described above in admixture with a pharmaceutically acceptable carrier or vehicle and optionally an adjuvant. Details on suitable formulations can be found in WO 00/20027.

Alternatively, the vaccine may be in the form of a nucleic acid vaccine (for details concerning this technology, cf. WO 00/20027). Thus, also part of the invention is an immunogenic composition for immunizing against HER-2 protein in a human comprising the vector described above in admixture with a pharmaceutically acceptable carrier or vehicle and optionally an adjuvant Also embraced by the scope of the present invention is a method for immunizing a human against autologous HER-2, the method comprising administering, to the human being, an immunogenically effective amount of
    the immunogenic variant of HER-2 protein described herein or an immunogenic composition comprising the variant, or
    the vector described herein or an immunogenic composition comprising said vector.

It is especially preferred that this immunization method (as well as the different means for immunization described herein) is used for treating or ameliorating cancer.

PREAMBLE TO THE EXAMPLES

The following exemplification utilizes the "104.1 molecule" (cf. SEQ ID NO: 2) which is an immunogenic analogue of the cancer associated HER-2 protein. However, it will be understood by the person skilled in the art that the general teachings of the present invention are applicable for other His tagged proteins, especially those produced recombinantly in insect cell systems.

The purification process consists of the following 4 general purification steps:

1. Diafiltration with buffer change of fermentation supernatant.

2. Immobilized Metal Affinity Chromatography (IMAC)

3. Gel filtration/Size Exclusion Chromatography (SEC)

4. Anion Exchange Chromatography (AIE)

There is additionally 2 virus clearance steps included in the currently preferred process, one virus inactivation step and one virus filtration step.

Diafiltration/Buffer Exchange

The diafiltration serves three purposes 1) to concentrate the substance "104.1" 2) to remove low molecular weight substances from the fermentation medium that could interfere with the subsequent capture step, such as metal ions and 3) to change buffer into a buffer more suitable for metal chelate chromatography (IMAC). Buffer exchange takes place in one or two steps. The first step is into 50 mM phosphate buffer pH 7.0; the second step into 50 mM phosphate buffer pH 7.5 is optional. If diafiltration is performed into pH 7.5, this pH sequence seems to be critical because going directly into pH 7.5 leads to precipitation of non-identified components from the insect cell fermentation medium. Concentration is mainly performed to reduce loading time in the subsequent IMAC and to reduce consumption of buffer in the buffer exchange step and is not found essential for the process, as the subsequent IMAC by nature is a concentrating process step. The concentration scale is presently about 5 times or to a total protein concentration of the medium not exceeding 3 mg/ml (preferably not exceeding 2 mg/ml), but experiments using 10 times concentration also seem to work when protein level does not become to high and it is expected that it is possible to go higher, such as 20 or even 25 times. Further concentration than the 5 times described in the protocol may improve the process, as it would decrease the loading time on the following IMAC column.

Sample Preparation for IMAC

The diafiltrate can prior to application to the IMAC column be prepared by adding imidazole to a final concentration of 0-10 mM, when imidazole is used in eluent buffer; if no imidazole (or a similar substance) is added, we have experienced co-purification of other proteins from the insect cells with 104.1.

On the other hand, when elution is made with L-Histidine, salt is added to the elution buffer instead. Furthermore, Tween 20 is added (after filtration) to a final concentration of 0.1% (v/v). Up to 5% can be applied for the IMAC step and higher concentration than 0.1% will lead to less dimer formation. Other detergents are also expected to be useful, obviously other Tween detergents (Tween 40, 60, 80 and 85).

IMAC

The substance 104.1 has a so-called His-tag in the N-terminus that has affinity for complexed divalent metal ions immobilized on the column matrix. Critical parameters are choice of divalent metal ion and choice of elution agent/method. $Ni^{2+}$, $Cu^{2+}$ and $Zn^{2+}$ can all be used as the chelating metal ion. However, $Zn^{2+}$ has provided good recovery and fewer impurities. For elution of captured 104.1 several strategies can be used. 1) Application of imidazole to the column 2) application of histidine to the column 3) application of high salt concentration buffer to the column, and 4) change of pH on the column.

The presently preferred process uses elution by application of 100 mM L-Histidine in one step. However, down to 50 mM can be used but the result is less concentrated 104.1 and lower recovery. It is also possible to use imidazole (applied as a 200 mM solution), and also this can be used at lower (down to 50 mM) concentrations with the same effect on recovery.

SEC

The example below describes that the SEC is run in TRIS buffer. However, phosphate seems to work as well, but TRIS is more suitable for the subsequent AIE than phosphate.

When using phosphate or a TRIS buffer containing salt, dilution of the SEC eluate is necessary before application on the AIE column in order to reduce the phosphate concentration, and this will not be necessary with a TRIS buffer only.

If the IMAC has been run in a Tween-20 concentration higher than 0.4%, it should be adjusted to <0.4% in the SEC, as the 104.1 protein does not bind to the AIE column if the concentration of Tween-20 is higher than 0.2%. This may differ when the AIE is run in other buffer systems.

Sample Preparation for AIE Chromatography

The relevant fractions from SEC are diluted in water, 1 volume eluate+3 volumes of water, to reduce the phosphate concentration when run in phosphate as it interferes with the AIE chromatography. This issue is also discussed in the SEC paragraph.

AIE Chromatography

The critical parameters are the pH and ionic strength of the sample and buffer systems.

If the SEC has been run in TRIS, the sample preparation (dilution in water) can be avoided and the loading volume (and loading time) will be reduced. When the AIE is run in TRIS buffer including salt, the AIE is diluted in TRIS buffer until an ionic strength below 3 mS/cm is reached.

Final bulk product is analysed by SDS-PAGE, western blotting (WB), ELISA, HPLC, visual inspection, $OD_{280}$, pH, *Limulus* Amoebocyte Lysate (LAL) and amino acid analysis. Intermediate products are analysed by SDS-PAGE, WB, ELISA and $OD_{280}$.

As will be apparent, the AIE is preferably performed as two consecutive steps, where a first step utilises a weak anion exchange matrix and a second step utilises a strong anion exchange matrix. It is contemplated, however, that the step using a weak AIE matrix can be moved so as to be introduced between the IMAC and SEC steps.

Example 1

Culturing of HER-2 Variant 104.1

Cell Line Production

A polyclonal culture of S2 *Drosophila melanogaster* cells was transfected with a pMT vector (DES® system, Invitrogen) containing the gene coding for the HER2 variant 104.1; the entire nucleic acid sequence of this pMT vector is set forth in SEQ ID NO: 1. The cells were in parallel transfected with a plasmid carrying a gene conferring hygromycin resistance enabling the usage of hygromycin for selection of transfected cells.

A limited dilution technique was used for isolation of single cell clones and a Master Cell Bank (MCB) was produced from the selected cell line.

HER2 Protein AutoVac Production

One vial from the MCB is resuscitated in a T-flask and propagated in shake flasks containing ExCell420 media (JRH) at 25° C. to obtain enough biomass for the inoculation of a bioreactor. A total of $45 \times 10^9$ cells is diluted into 3000 mL with ExCell 420 supplemented with 4 mM Glutamine, 0.1% Pluronic F68, and 0.5 mL/L PD30 antifoam. The 3000 mL are used to inoculate an Applikon bioreactor (7 L working volume) where the culture grows for 3 days at 25° C., $dO_2$=50% (100%=air saturation), pH=6.5±0.1 (adjusted with 5% $H_3PO_4$ and 0.5 M NaOH), and stirred at 170 rpm.

This culture is diluted with ExCell 420 supplemented with 4 mM Glutamine, 0.1% Pluronic F68, and 0.5 mL/L PD30 antifoam to a total cell concentration of $15 \times 10^6$ cells/mL and used for inoculation of a 15 L working volume Applikon Bioreactor maintaining 25° C., $dO_2$=50% (sparging with pure oxygen), pH=6.5±0.1 (adjusted with 5% $H_3PO_4$ and 0.5 M NaOH), and stirred at 142 rpm. The culture is continuously diluted with ExCell 420 supplemented with 4 mM Glutamine and 0.1% Pluronic F68 until a total volume of 10 L is reached. The dilution rate is adjusted daily to prevent the cell number to drop below $15 \times 10^6$ cells/mL. PD30 antifoam is added manually to the culture to maintain a total concentration of 0.5 mL/L.

When filling is completed, perfusion is initiated at 1 RV/day (reactor volumes per day) using the BioSep cell (AppliSens) acoustic retention device to prevent cell loss with the removed media. At a cell concentration of $30 \times 10^6$ cells/mL, the culture is induced by addition of a total of 2 μM $CdCl_2$ (10 mM stock) to the culture and to the medium reservoir.

The fermentation medium is harvested, centrifuged to obtain a cell free supernatant, and filtrated through a PALL filter 0.8/0.22 μm. The resulting sterile supernatant is either stored at −80° C. until use (storage up to three months at −80° C. has not produced detectable stability problems) or stored at 4° C. without for up to one week (also without any detectable degradation of the protein).

The culture is terminated 10 days post induction and the residual culture media in the bioreactor is discarded.

Example 2

Diafiltration/Concentration and Buffer Change

Before use, the fermentation supernatant from Example 1 is, if kept at −80° C., thawed slowly at 4° C. over night (the last 3 to 4 hours can be performed in cold water), and thereafter stored for a maximum of 3 days at 4° C. Otherwise, the fermentation supernatant is used directly.

The fermentation supernatant is centrifuged in a Sorvall RE 5C Plus Centrifuge in SCA3000 tubes at 10,000 rpm for 15 min, at 4° C.

Diafiltration is performed in a cold room at 5±3° C. on a Pro-Flux M12 (Millipore) with a Pellicon 2 Cassette filter 30 K 0.5 $m^2$ (Millipore, Cat# P2B030A05). The filter is before use stored in 0.1 M NaOH. Before diafiltration the filter is therefore thoroughly washed through with milli-Q water: The standard reservoir is filled with milli-Q water (3 L) and washed with water through the filter until 200 ml is left in the reservoir. This procedure is repeated 3 times until a total of 12 litres has passed through the filter. Now, diafiltration can be instigated:

A maximum of 15 L fermentation supernatant is concentrated about 5 times or to a total protein concentration of the medium not exceeding 2 mg/ml, as measured by a calorimetric method.

The recirculation pump is started. The backpressure valve should be partly locked, to give an outlet pressure that shows back pressure (e.g. 0.2 bar). The pump speed is adjusted to 30-50%. The pressure difference should show 0.7-1.2 Bar, as this is when the filter's maximum capacity is used and flow over filter correspond to 3-4 L/min (e.g. Outlet P=0.2 Bar, Inlet P=1.0 bar, ΔP=0.8). Inlet pressure should show max 1.4 bar considering tubing life and performance. If a higher inlet pressure is desired, the recirculation pump pressure can be elevated (%) or the mechanical pressure on the tubing could be elevated by applying higher pressure on the tubing (scale 0-5). When the back pressure valve is closed, a higher inlet and higher outlet pressure is received. The back pressure valve should never be completely shut.

Subsequently, the concentrated fermentation supernatant is subjected to buffer exchange in one or two steps, first using 10 volumes 50 mM $Na_2HPO_4/NaH_2PO_4$, pH 7.0, and then in the optional second step by 10 volumes 50 mM $Na_2HPO_4/NaH_2PO_4$, pH 7.5: The standard reservoir on the ProFlux M12 Millipore apparatus is filled with buffer to a total volume of 3 L and also the side reservoir is filled with buffer. The setting on the apparatus is the same as when concentrating the sample.

The volume of the buffer changed sample (Vb) is measured and a sample is taken out for SDS-PAGE (Sb). The concentrated buffer changed sample is portioned into 11 ml and 50 ml lots and frozen quickly to −80° C.

Analysis of the Diafiltrate pH and ionic strength is measured to assure efficiency of the buffer exchange.

Total protein concentration is estimated spectrophotometrically at 280 nm in a 1 cm cuvette. A 10 times diluted sample (diluted in 50 mM sodium phosphate buffer pH 7.5) with 50 mM sodium phosphate buffer pH 7.5 is used as reference (using the approximation $Abs_{280}$ of 1=1 mg/ml total protein). The total protein concentration can additionally be measured by a calorimetric Bradford method (BioRad). The specific concentration of variant 104.1 is measured by ELISA and the diafiltrate is furthermore analysed by SDS-PAGE, silver stained and WB-ECL detection.

Remarks to the Diafiltration Step

It is important to start the buffer exchange at pH below 7.1 before changing to pH 7.5. Otherwise, residual components from the fermentation medium precipitate.

Diafiltered samples have been stored at −80° C. for several months without change in performance in the quantitative HER-2 ELISA. However, when thawed, even short exposure to 37° C. and 54° C. dramatically decreases the performance of the diafiltrate in the same ELISA. When kept at 0° C. (ice/water) and 4° C. after thawing from −80° C., the performance in the ELISA of the diafiltrate is stable for up to at least 4 hours.

After diafiltration, it is convenient to inactivate any virus that might be present in the diafiltrate. To do this, samples are thawed at 2-8° C. and pooled, subsequently filtered through 1.0/0.45/0.2 μm filters, where after 50% Tween-20, and TnBP are added to a final concentration of 2% and 0.3%, respectively. The solution is kept at 2-8° C. for 16-20 hours while gently stirring. The solution is then 0.2 μm filtered prior to the subsequent IMAC chromatography step (Example 3).

Example 3

IMAC

The general chromatographic principle for IMAC is affinity between a "tag" on the protein and a metal ion chelate complex on the column matrix. The chromatographic matrix is POROS 20MC or, preferably, 50MC (both from Applied Biosystems) and the chelating metal ion is $Zn^{2+}$. The 104.1 molecule is provided with a His-tag and the buffer system for binding of the His-tag to the column matrix is 50 mM $Na_2HPO_4/NaH_2PO_4$, 0.1% Tween20, pH 7.5.

2-4 mg 104.1 per ml column material is loaded and subsequently eluted using 100 mM L-Histidine, 50 mM $Na_2HPO_4/NaH_2PO_4$, pH 7.5, 0.1% Tween20. Alternatively, when eluting with 200 mM Imidazole, the buffer system for binding also contains 5 mM Imidazole.

Instrument: VISION Work Station (Applied Biosystems).

Software: Data analysis software for Vision, BioCAD 700E, version 3 series software, Perseptive Biosystem.

Detection: UV absorbance at λ=280 and 220 nm.

Conductivity: 0-200 mS pH calibrated at: 7.0 and 10

Temperature: The procedure was made with buffers and column at room temperature (20-24° C.) and loading of sample on ice and fraction collection at 10° C.

Sample Preparation

To the diafiltrate containing the 104.1 molecule, 800 mM imidazole is added to a final concentration of 5 mM imidazole when an Imidazole containing buffer is used for elution in the IMAC, whereas Tween-20 is added to a final concentration of 0.1% (v/v) when L-histidine is used for elution in the IMAC. Immediately before application to the column the sample is filtrated by vacuum through a 0.22 μm filter. The sample is kept at 5±3° C. (preferably 4° C.) until application to the column where it is held on ice when applied. Handling time at room temperature should be minimized.

Column

POROS 20 MC or 50 MC (preferred) in a 16×100 mm (20.1 ml) PEEK column (Applied Biosystems) packed at 2000-2500 psi—other columns depending on the scale of the purification procedure, are equally useful.

Column Charge (Strip-Charge) Program

Flow: 10 ml/min.
1. 5 CV of 50 mM $NaPO_4$ (abbreviation for $NaH_2PO_4/Na_2HPO_4$) pH 7.5, 0.1% Tween-20 (strip).
2. 5 CV $H_2O$ (Milli-Q).
3. 40 CV 100 mM $ZnCl_2$, pH 4.5.
4. 40 CV $H_2O$ (Milli-Q).
5. 20 CV 50 mM $NaPO_4$ pH 7.5, 0.1% Tween-20.

The column should be charged before each run.

Chromatography Program

Flow rate 30 ml/min, loading 5 ml/min.

Fraction collection size 9 ml, and 5 ml at the elution peak with 100 mM L-histidine (or, where applicable, at elution peak with 200 mM imidazole). Collect in a cooled (10° C.) fraction collector.

The solution containing the virus inactivated diafiltrate is loaded on to the column at 4° C. and washed with 20 CV 50 mM $NaPO_4$ pH 7.5, 0.1% Tween 20, 0.5 M NaCl followed by 5 CV of 50 mM $NaPO_4$ pH 7.5, 0.1% Tween 20 prior to elution with 50 mM $NaPO_4$ pH 7.5, 0.1% Tween 20, 100 mM Histidine.

Figure 1:
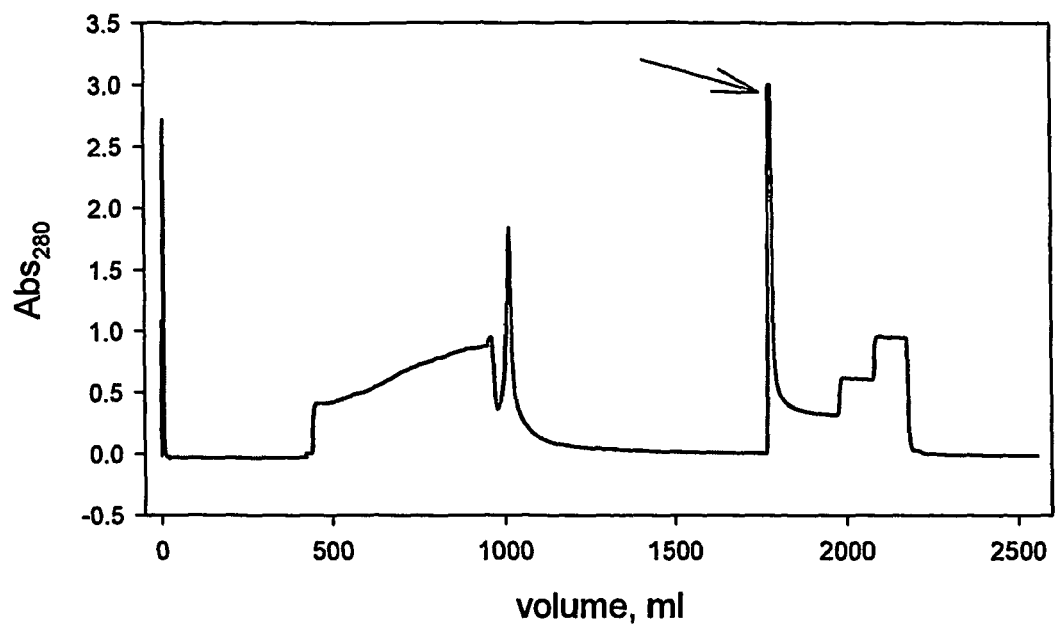
FIG. 1: Chromatographic profile of the IMAC.

Pool the fractions from the eluted peak from chromatogram (cf. FIG. 1). Begin pooling at peak start and collect a total of 50 ml (or 1.5 column volumes) or pool fractions based on SDS-PAGE/WB results or ELISA to a total of 50 ml. This pool can be saved over night at 5±3° C. or carried on to SEC straight away. Storage of pool up 7 days at 5±3° C., −20° C. and colder than −70° C. has shown no loss in total protein after filtration through 0.22 μm filter when analysed on SDS PAGE and WB-ECL.

Sanitization of Column

Wash the column with 5 CV 1 M NaOH, 2 M NaCl, followed by 10 CV of water. If further sanitization is needed see the RSP from the manufacturer. The column is stored in 30% EtOH at 5-30° C.

Analysis of IMAC Intermediate

Start material, flow through and eluted fractions are analysed by WB-ECL and SDS-PAGE/silver stained.

Analysis of IMAC Pool

The pool is analyzed by WB-ECL and SDS-PAGE/silver stained, HPLC and $OD_{280\ nm}$ (on 10 times diluted sample). The specific 104.1 concentration is determined by ELISA.

Example 4

SEC Gel Filtration Chromatography

The gel filtration step is run in mM Tris, 0.1% Tween-20, pH 7.5, but 50 mM $Na_2HPO_4/NaH_2PO_4$ can substitute the Tris as buffer system. Fifty ml from IMAC of Example 3 is loaded by Superloop (Pharmacia) on a Superdex 200 prep grade matrix.

Instrument: BioCAD 700E Work Station for Perfusion Chromatography equipped with a semi-preparative flow cell to reduce the back pressure on the column.

Software: Data analysis software for Vision, BioCAD 700E, version 3 series software, Perseptive Biosystem.

Detection: UV absorbance at $\lambda=280$ and 220 nm.

Conductivity: 0-200 mS pH calibrated at: 7.0 and 10

Temperature: Buffers and column are room temperature (20-24° C.) and the sample is loaded directly from 4° C. Fractions containing the monomer 104.1 should be moved to 4° C. directly after collection if the collector is not cooled.

Sample Preparation

The Pool from IMAC in buffer, 50 mM $Na_2HPO_4/NaH_2PO_4$, 0.1% Tween20, 100 mM L-Histidine (or 200 mM Imidazole), pH 7.5, requires no special preparation. The sample should be kept cool (5±3° C.) until loading.

Column

Superdex 200 prep grade, packed in Pharmacia column XK 50×960 mm (1884 ml) at 15 ml/min as final flow rate. Load maximum 50 ml.

Chromatography Program

General flow rate 8 ml/min, load 5 ml/min.

Fraction size 9.0 ml

1. Equilibration 1.5 CV 20 mM Tris, 0.1% Tween-20, pH 7.5
2. Load: via 50 ml Super Loop, 5 ml/min
3. Elution 1.2 CV 20 mM Tris, 0.1% Tween-20, pH 7.5

The fractions from the monomer peak (cf. FIG. 2) are pooled by comparing gel and/or SE/RP-HPLC results to obtain a pure product (approximately 130 ml). This pool can be saved over night at 5±3° C. or carried on directly to the AIE chromatography of Example 5. Storage of pool up to 7 days at 5±3° C., −20° C. and colder than −70° C. has shown no loss in total protein after filtration through 0.22 µm filter when analysed by SDS PAGE and WB-ECL.

Sanitization and Cleaning of Column

The column is cleaned by running 0.5 NaOH in the reversed flow direction for 1-2 h at 6.5 ml/min (20 cm/h) followed by 3 bed volumes of buffer. For sanitization run 0.5-1.0 NaOH in reversed flow direction, 13 ml/min (40 cm/h) for 30-60 min followed by 3-5 bed volumes of sterile buffer. The column is stored in 20% ethanol at 4-8° C. For additional information confer manufactures manual.

Analysis of the SEC Intermediate

Start material and eluted fractions are analyzed by WB-ECL, SDS-PAGE/silver stained and SE/RP-HPLC.

Analysis of SEC Pool

The pool is analysed by WB-ECL and SDS-PAGE/silver stained, HPLC and $OD_{280\ nm}$. The specific 104.1 concentration is determined by ELISA.

Remarks to SEC

Make sure that the sample is kept at 5±3° C. between IMAC and loading from the Superloop.

If the fraction collector is not cooled (10° C.) make sure that fractions are moved to cold room/fridge immediately after the collection.

When the column is frequently used, a constant flow (0.2 ml/min) of 20 mM Tris, pH 7.5, 0.1% Tween 20 is applied to the column (alternatively 50 mM $Na_2HPO_4/NaH_2PO_4$ is used instead of 20 mM Tris and if that is the case, Tween-20 is used at 0.5%).

Example 5

AIE Chromatography

First Optional Step

Anion Exchange Chromatography is first optionally performed on a Poros 50PI matrix column. The column is equilibrated with 20 mM Tris HCl, 0.1% Tween 20 at pH 7.5. Post-equilibration, a sample is retained for bio burden testing.

The SEC eluate is loaded onto the column at 4° C. and the column washed with 20 CV 20 mM Tris HCl, 0.1% Tween 20 at pH 7.5 followed by product elution with 20 mM Tris HCl, 250 mM NaCl, 0.1% Tween 20 pH 7.5. The product pool is 0.2 µm filtered, analysed by OD280 nm, 104.1 ELISA, RP-HPLC and SE-HPLC, and stored at 2-8° C. for up to 3 days.

The Poros 50PI column is flushed with $H_2O$ (milli-Q) and cleaned with 10 CV of 2 M NaCl, 1 M NaOH before storage in 20 mM NaOH. It is sanitised with 5 CV of 0.5 M NaOH and flushed with $H_2O$ (milli-Q) before equilibration and subsequent re-use.

Mandatory Step

Anion exchange chromatography is performed at pH 7.5 (20 mM TRIS), preferably on a strong anion exchange perfusion matrix POROS 50HQ (Applied Biosystems) in a PEEK 4.6×100 mm (1.662 ml) column. 104.1 is eluted in 200 mM NaCl.

Instrument: VISION Work Station for Perfusion Chromatography.

Software: Data analysis software for Vision, BioCAD 700E, version 3 series software, Perseptive Biosystem.

Detection: UV absorbance at $\lambda=280$ and 220 nm.

Conductivity: 0-200 mS pH calibrated at: 7.0 and 10

Temperature: The procedure was made with buffers and column at room temperature (20-24° C.) and loading of sample from ice. The fraction collector was cooled to 10° C.

Sample Preparation

If the first optional AI step is omitted, the SEC intermediate may be diluted 1+3 (to 25%) in water containing 0.1% Tween-20 under gentle magnetic stirring. Otherwise, the POROS 50PI eluate is diluted in 15 volumes 20 mM Tris HCl, 0.1% Tween-20 at pH 7.5 to reduce conductivity. The sample should be kept cool (5±3° C.) until and during loading.

Column

POROS 50HQ is packed in a 4.6×100 mm (1.662 ml) PEEK column (Applied Biosystems) at 2000-2500 psi.

Chromatography Program

General flow rate 10 ml/min, load sample 5 ml/min.

Fraction size: 9 ml during sample load, 1 ml during $1^{st}$ elution step, and 5 ml during $2^{nd}$ elution step Anion Exchange Chromatography is performed on a Poros 50HQ matrix column at 4° C. The column is equilibrated with 20 mM Tris HCl, 0.1% Tween 20 at pH 7.5. Post-equilibration a sample is retained for bio burden testing.

The sample is loaded onto the column and the column washed with 10 CV 20 mM Tris HCl, 0.1% Tween 20 at pH 7.5 and 10 CV 20 mM Tris HCl, 20 mM NaCl, 0.1% Tween 20 at pH 7.5 followed by product elution with 20 mM Tris HCl, 200 mM NaCl, 0.1% Tween 20 pH 7.5.

The fractions from the elution peak (cf. FIG. 3) are pooled by comparing gel results to obtain a concentration of more than 2.5 mg/ml or $OD_{280nm}$, more than 2.5. The fractions can be kept over night at 5±3° C. before pooled. Storage of pool up to 7 days at 5±3° C., −20° C. and colder than −70° C. has shown no loss in total protein after filtration through 0.22 μm filter when analysed by SDS PAGE and WB-ECL.

Sanitization of Column

Wash the column with 10 column volumes (CV) of 1 M NaOH, 2 M NaCl, followed by 20 CV of water. If further sanitization is needed confer manufacturer's manual. The column is stored in 30% ethanol at 5-30° C.

Analysis

Start material, flow through and eluted fractions are analysed by WB-ECL and SDS-PAGE/silver stained.

Analysis of AIE Pool

The pool is analysed by WB-ECL and SDS-PAGE/silver stained, Appearance and description, pH, HPLC, LAL and $OD_{280\ nm}$ (use 3 times diluted sample). The specific 104.1 concentration is determined by ELISA.

Remarks to AIE

If the SEC intermediate is diluted less than 1+3 (25%) 104.1 is detected in the run-through from the AIE due to interference from the phosphate buffer.

Up to 25 mg 104.1 has been applied to the AIE column without detectable amounts of 104.1 in the run-through.

Optional Virus Filtration

Virus filtration and the subsequent dilution and filling of drug substance take place in a Class 100 environment. Prefiltration purified bulks from one or more Poros 50HQ runs are removed from frozen storage and thawed at 2-8° C. They are then 0.1 μm filtered and passed through a Planova 20N virus filtration membrane. The filter is retained for integrity testing. The virus filtered material is adjusted to a concentration of 2.5-3.0 mg/ml by measurement of OD280 nm.

Storage of Final Bulk Product

The final bulk product is stored at temperatures colder than −70° C. in a polypropylene container or CZ vial after filtration through 0.22 μm filter.

The product thus obtained has a purity which is suitable for clinical use.

The invention claimed is:

1. A nucleic acid fragment that encodes a polypeptide that comprises the amino acid sequence set forth in SEQ ID NO: 2, residues 17-677.

2. The nucleic acid fragment according to claim 1, which is a DNA fragment.

3. A vector carrying the nucleic acid fragment according to claim 2.

4. The vector according to claim 3, which is capable of autonomous replication.

5. The vector according to claim 4 being selected from the group consisting of a plasmid, a phage, a cosmid, and a virus.

6. The vector according to claim 3, which is an expression vector.

7. The vector according to claim 6, comprising in the 5'→3' direction and in operable linkage, a promoter for driving expression of the nucleic acid fragment, a nucleic acid sequence encoding a leader peptide enabling secretion of or integration into the membrane of the encoded polypeptide, and the nucleic acid fragment.

8. A transformed host cell carrying the vector of claim 3.

9. A transformed host cell carrying the vector of claim 6.

10. A stable cell line which carries the vector according to claim 6.

11. A composition comprising the vector according to claim 6 in admixture with a pharmaceutically acceptable carrier or vehicle and optionally an adjuvant.

12. A nucleic acid fragment that encodes a polypeptide that consists of the amino acid sequence set forth in SEQ ID NO: 2, residues 17-677.

* * * * *